United States Patent
Pickover (10) Patent No.: US 7,505,981 B2
(45) Date of Patent: Mar. 17, 2009

(54) METHOD FOR EVOLVING EFFICIENT COMMUNICATIONS

(75) Inventor: Clifford Alan Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 367 days.

(21) Appl. No.: 10/939,823

(22) Filed: Sep. 13, 2004

(65) Prior Publication Data

US 2006/0057079 A1    Mar. 16, 2006

(51) Int. Cl.
G06F 17/00    (2006.01)
G06F 19/00    (2006.01)

(52) U.S. Cl. .................... 707/100; 707/3; 424/50

(58) Field of Classification Search .......... 707/1, 707/3, 100; 348/586; 424/50
See application file for complete search history.

(56) References Cited

U.S. PATENT DOCUMENTS

| | | | | |
|---|---|---|---|---|
| 5,862,223 A | * | 1/1999 | Walker et al. | 705/50 |
| 6,288,753 B1 | * | 9/2001 | DeNicola et al. | 348/586 |
| 6,471,521 B1 | * | 10/2002 | Dornbush et al. | 434/322 |
| 6,631,377 B2 | * | 10/2003 | Kuzumaki | 707/10 |
| 7,069,028 B2 | * | 6/2006 | Natsuno | 455/466 |
| 2003/0092455 A1 | * | 5/2003 | Natsuno | 455/466 |
| 2004/0029092 A1 | * | 2/2004 | Orr et al. | 434/354 |
| 2004/0210550 A1 | * | 10/2004 | Williams et al. | 707/1 |
| 2005/0086189 A1 | * | 4/2005 | Noble | 706/50 |
| 2006/0036563 A1 | * | 2/2006 | Wu | 706/59 |

* cited by examiner

Primary Examiner—Etienne P LeRoux
Assistant Examiner—Cindy Nguyen (57) ABSTRACT

A method and service method facilitate collaboration with, communication of, and access to information, particularly in an education environment. One or more sets of respondents are selected to respond to one or more queries from a querent by using a strength value between the querent and one or more of the respondents in the set. One or more responses to the query are received from one or more of the respondents. The strength values of the respective respondent are updated by an assessment of the response. Updated connections for future queries iteratively evolved, based at least in part on the updated strength values. The updated connections are stored in a data structure such that a computer can access the data structure to obtain useful responses to the future queries. In some instances, the steps may be performed as a service and a fee may be charged.

3 Claims, 7 Drawing Sheets

| Vector # | P₁ | P₂ | Strength | Topic | Cost |
|---|---|---|---|---|---|
| 1 | Lou | Cliff | (+50, +2, +1) | Pets | 5¢ |
| 2 | John 111 | Cliff | (-2, +5, +1) | Computers | $1.00 |
| 3 | Marie 70 | Lou | (+10, -5, -1) | Golf, Cat | 10¢ |
| 4 | Lou | Cliff | (+10, -1, -5) | Physics | 20¢ |
| 5 | Cliff | Barb | (+2, +1, 3) | Soccer | $1.00 |

METHOD FOR EVOLVING EFFICIENT COMMUNICATIONS

FIELD OF THE INVENTION

This invention relates to systems and methods used to facilitate collaboration, communication, access, and flow of knowledge. More particularly, the invention helps users obtain answers to questions and become more productive, especially in a learning environment.

BACKGROUND OF THE INVENTION

In this fast-paced and complex world, it is difficult to find answers to questions in a variety of fields. No single individual can be an expert in all areas of knowledge, and a single individual may have to solve many different problems while on the job or at home. Currently, it is common for a technical support desks to help computer users solve problems. Unfortunately, such a help desk typically provides information on only a limited range of topics. For example, a user does not typically use a single help desk to obtain an answer to questions about English usage, a computer graphics application, a computer business application, and pets. Additionally, help desks are sometimes expensive to use, maintain, staff, and support. In the hiring process, most help desk managers look for a high degree of technical aptitude, the ability to communicate well and empathize with the customer's (user's) situation. Thus, the technical support representative's level of emotional intelligence and specific expertise, but not necessarily their level of general knowledge, is critical to success.

Sometimes users seeking answers use computer bulletin boards to obtain answers to questions. However, bulletin board usage often requires a user to understand beforehand which precise bulletin board to use, and the posting process often does not automatically facilitate the building of persistent relationships between people, and is not optimized for obtaining high-quality and rapid answers. The communications connections between querent and responder are not always easy to automatically re-access at a later point in time.

PROBLEMS WITH THE PRIOR ART

Often people need to find a particular type of professional service, e.g., legal, accounting, engineering, artistic, etc. and have no contacts in these areas. Using the prior art, it is difficult to find and/or evaluate these professional services using the prior art.

Individuals often spend significant time searching for information to help solve problems in both business and personal life. Help desks are limited and expensive to maintain. Bulletin boards may not have topically expertise specific to a query, can be hard to locate, and don't necessarily provide a way to determine information accuracy. Bulletin boards and help desks often do not automatically facilitate the building of persistent relationships between people and may not be optimized for obtaining high-quality and rapid answers.

Today, people sometimes get quick answers simply by e-mailing questions to friends. However, a query may be about a topic for which the circle of friends has no extensive knowledge. One's limited circle of friends may not be sufficient for getting answers, and a person cannot frequently find experts willing to help solve a problem.

Timing can also be a problem in the prior art. A circle of friends or contacts may not be available or easy to contact when the querent needs an answer to a query. Also, the communications connections between querent and responder are not automatically re-accessable at a later point in time.

ASPECTS OF THE INVENTION

An aspect of this invention is an improved system and method to facilitate collaboration with, communication of, and access to information.

An aspect of this invention is an improved system and method for receiving one or more answers associated with queries.

An aspect of this invention is an improved system and method to facilitate collaboration with, communication of, and access to expert information.

An aspect of this invention is an improved system and method to facilitate collaboration with, communication of, and access to information provide by a general set of responders.

An aspect of this invention is an improved system and method to facilitate collaboration with, communication of, and access to information provide by a general set of responders and establishing a persistent relationship with one or more of the respondents.

An aspect of this invention is an improved system and method to facilitate collaboration with, communication of, and access to information provide improved connectivity and access to a general set of responders.

An aspect of this invention is an improved system and method to facilitate collaboration with, communication of, and access to information provide by a general set of responders in an education environment.

An aspect of this invention is an improved system and method to determine aspects about one or more responders in a set of responders.

SUMMARY OF THE INVENTION

Principles of the invention provide techniques for evolving efficient communications. In one aspect, a computerized method for data access include the steps of selecting one or more sets of querent and one or more of the respondents in the set; receiving one or more responses to the query from one or more of the respondents; updating the strength values of the respective respondent by an assessment of the response; iteratively evolving updated connections for future queries, based at least in part on the updated strength values; and storing the updated connections in a data structure such that a computer can access the data structure to obtain useful responses to the future queries.

In another aspect, an exemplary method of providing a service for accessing responses to queries includes the steps of receiving one or more queries from one or more querents; selecting one or more sets of respondents to respond to one or more of the queries by using a strength value between the querent and one or more respondents; updating the strength values of the respective respondent by an assessment of the response; iteratively evolving updated connections for future queries, based at least in part on the updated strength values; storing the updated connections in a data structure such that a computer can access the data structure to obtain useful responses to the future queries; and charging a fee for, at least, access to the database for purposes of obtaining the useful responses.

BRIEF DESCRIPTION OF THE FIGURES

The foregoing and other objects, aspects, and advantages will be better understood from the following non-limiting

DETAILED DESCRIPTION OF THE INVENTION

Information is critical to today's commercial organizations and our personal lives. Typically, we have friends, or friends of friends, who may be able to easily answer our questions, but it is often difficult to know who to ask or how and when to access these people. The system and method described herein allows a user to work with a virtual single point of contact and evolve useful communication connections between a querent and a network or set of responders so that the a querent is likely to get a satisfactory answer to a question. In one preferred embodiment, the system and method described herein creates a "group mind" that can be used to solve problems that any individual alone could not solve. In one preferred embodiment, the invention randomly queries one or more potential responders that may or may not be known to the querent. The invention identifies/creates connections that develop, form, and/or are updated with a set of the respondents so that the set can be queried later more efficiently, e.g., useful communication channels evolve. The communication channels improve with iteration.

Some non limiting uses of the invention are in: educational settings involving students, corporations, and any arena in which individuals are seeking information.

In a preferred embodiment, the invention enables a querent (e.g., a querent seeks information or an answer to a question) to query one or more known or unknown potential respondents over a network. The system establishes a communication connection between the querent and one or more potential responders, sends the query(ies) between querent and one or more potential responders, receives a response from one or more responders, assesses the quality of one or more of the responses, changes one or more connection characteristics between querent and responders, and selects between potential responders based on a value associated with the connection between querents and responders for a given query(ies).

Computing systems, such as the one described here, are used to facilitate a flow of questions, answers, ideas and knowledge. The ThinkWeb (TW) allows people to be more productive, get answers to questions, collaborate, and in some sense become part of a "group brain" composed of several individuals whose composite knowledge is greater than a single member's knowledge. In one aspect, the TW can query random potential responders and evolve a useful set of connections for communications.

Consider a user who has a vast number of possible communication connections he can make with other people for the purpose of obtaining an answer to a question. This set of connections may be imagined as an octopus, with the center of the creature representing a user, and the various tentacles or tendrils representing the possible connections that may be made with other people, groups of people, or software agents capable of responding to queries. The challenge is knowing how to form, maintain, manage, and optimize these tendrils for obtaining answers to questions.

When first invoking the TW a user may optionally specify several areas of interest, for example: Banking, Automobiles, Telecommunications, Future Technology, Linux, Life Sciences, Computer Art, Fractals, and Software, Hardware, Visionary Ideas, Programming, Invention, Hobbies, World Wide Web, News, and so forth. Alternatively, the user need not specify any areas of interest.

In one embodiment, when the user invokes the TW, a TW client sends out "random" tendrils (i.e. connections) to a number, n, of potential responders (set or sets of responders) who may be interested in the same general topic areas. A user asks a question or tosses out an idea, and the n members of this virtual team (set of responders), which can be created on the fly, have an opportunity to give advice, share news items, brainstorm about inventions, and so forth. Often, not everyone will respond to a user's challenge or question.

However, if the user likes the particular advice from a person encountered using the TW, the connection (tendril) to this person is given a different status or weighting. Thus there will be a connection status associated with each of the connections. In a preferred embodiment, the connection status changes over time for one or more of the connections, i.e., the connection status changes depending on a number of status factors, e.g., time of response, quality of response, financial cost of response, level of a respondent in an organization (corporation, college), etc. Further note that the status for each connection/tendril can be defined by status attributes, e.g., question subject.

The user can indicate a favorable reaction to a response in many ways. In one preferred embodiment, the user may select a "helpful" button that increments a "usefulness" counter for that person. In preferred embodiments, connection status is used to determine future uses of the connection. For example, the connection status of a connection might determine whether a particular connection is used for a future query. This incrementing can be used to ensure a user's next invocation of the ThinkWeb tends to include people with incremented values in one's personal network of potential responders.

When used inside a company, the tendrils may traverse company divisions and have an initial random component that connects the user to randomly chosen potential responders in order to facilitate diverse ideas, viewpoints, and interaction of diverse skill sets. The TW may also learn and optimize the tendril connections automatically without the user having to press a "helpful" or "useful" button. For example, the system may suggest connections and people based on an assessment of people's skills and history of responding in certain topic areas to other querents or based on the number of increments a person has received by others. The system may reward those responders who provide useful advice. For example, a reward might be monetary or favorable employee evaluation. The system may allow users to visualize the tendrils in interesting ways, for example through a network diagram displayed on computer display in which color indicates those connections or tendrils that have yielded useful information flow.

The system encourages collaboration, serendipity, and new ideas. The TW is also highly practical, allowing the user to quickly get answers to questions and spend more effective time on those items for which the group brain (i.e. collection of members in connected together via the TW) has no fast answers.

Too many tendrils may lead to chaos; too few leads to unanswered questions and a less diverse skill set. Analysis tools can search for optimal and interesting routes through the tendrils. A user's ThinkWeb may metastasize into the user's partner's web, gaining tendrils from neighbors that may be useful. In other words, a responder in a user's TW network of potential responders also has his own responders whom a user may query.

This system and method also has implications for social and learning networks and how they form when one company absorbs another company. In these instances, the TW's tendrils may evolve in interesting ways. For example, when two separate TW networks of communication are made available, for example, through the merging of two groups, company departments, or companies, tendrils will begin to form between the two webs, thus automatically uniting people in the two companies as communications begin to flow between people.

The system and method may be used to determine trustworthiness of individuals or organizations. For example, if an individual is constantly "decremented" using the weighted tendril approach, this may mean that a person in an organization or classroom is often providing incorrect answers. Failsafes may be implemented to prevent a malicious use of this feature. For example, if one individual is constantly decrementing a variety of responders, this may mean that the user is too harsh or critical and, thus, his collection of increment and decrements may be weighted less when determining a respondent's overall rating.

A service bureau may run the TW for companies. In other words, a service bureau may software management tools, maintain the various networks between people, discover areas of expertise in a company, discover area of insufficient communication in teams, and charge a fee for this service based on various criteria.

Figure 1:
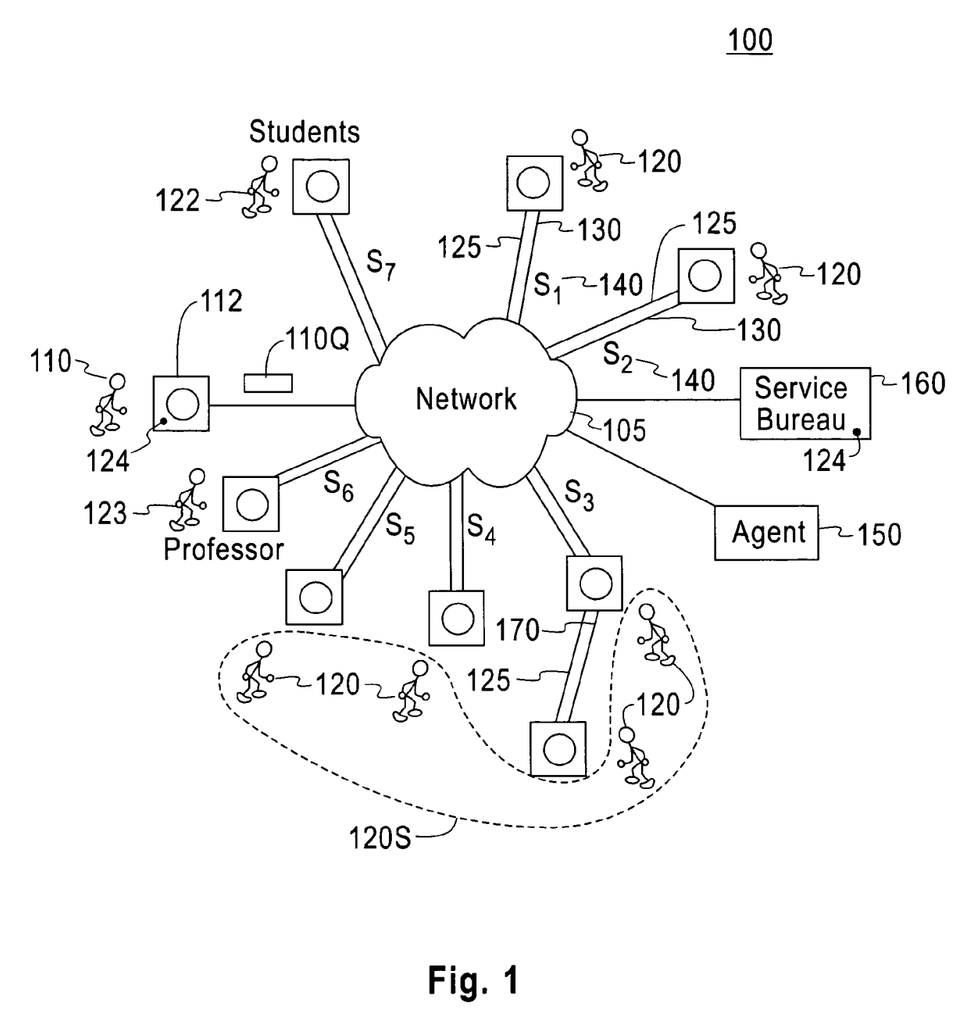
FIG. 1 is a block diagram on one preferred embodiment of the present invention, ThinkWeb (TW).

FIG. 1 shows a typical TW comprising a querent 110, a potential set of responders 120S, (typically 120) which may be other people, groups of people, or software agents capable of responding to a query 110Q, strength paths (i.e. communication connections or tendrils) 130 that link the querent 110 and potential responder 120, and a strength $S_n$ 140 that determines the strength of the association between querent 110 and responder 120.

In an educational setting, querents and responders may include teachers, such as professor 123, and students 122. The strength paths 130 may be an association between querent 110 and potential responder 120 stored as a vector in a database 124 that resides on a user's client computer 112 or on another computer 124, such as a service bureau computer 124. (The computers (112, 124) can be any general purpose computer.) For example, the strength 140 between querent 110 and responder 120 may increase if the responder provides a useful or high-quality answers as judged by the querent 110 or by a TW software agent 150, or by others. The software agent 150 may reside in the service bureau 124, at the querent's computer 112, or on another computer attached to the network. As the TW is used, those responders with higher strength values 140 may be favored in subsequent queries in order to increase the likelihood of receiving a high-quality response. In other words, if S2>S3, then the next time a querent asks a question, the responder associated with S2 may be asked instead of the responder associated with S3. Note that the strength 140 of the connection 130 may vary with the query 110Q. For example, a connection 130 might have different strength 140 for a query 110Q about history than for a query 110Q about biology. Alternatively, strengths 140 can change between the querent and responder over time for the same topic or different topics because the evaluation of the responder changed over time.

A service bureau 160 may run the TW and provide this as a service. Potential responders 120 may themselves have strength paths 170 to their own network of potential responders. For example, a first responder 120 would become a querent 110 to a second set of responders ("second-level responders") 120, who in turn may be querents to a third set of responders ("third-level responders") 120, and other higher-level respondents. It is initially noted that the TW environment is presented for illustration purposes only, and is representative of countless configurations in which the invention may be implemented. Thus, the present invention should not be construed as limited to the environment configurations shown and discussed herein.

The collection or responders and users are united by a computer network 105, such as the Internet or internal company network. Physical connections 125 between responders 120 and querent 110 may be provided by standard communication networks such as a wired Internet connection, a wireless connection, fiber optic, and/or a phone line.

Figure 2:
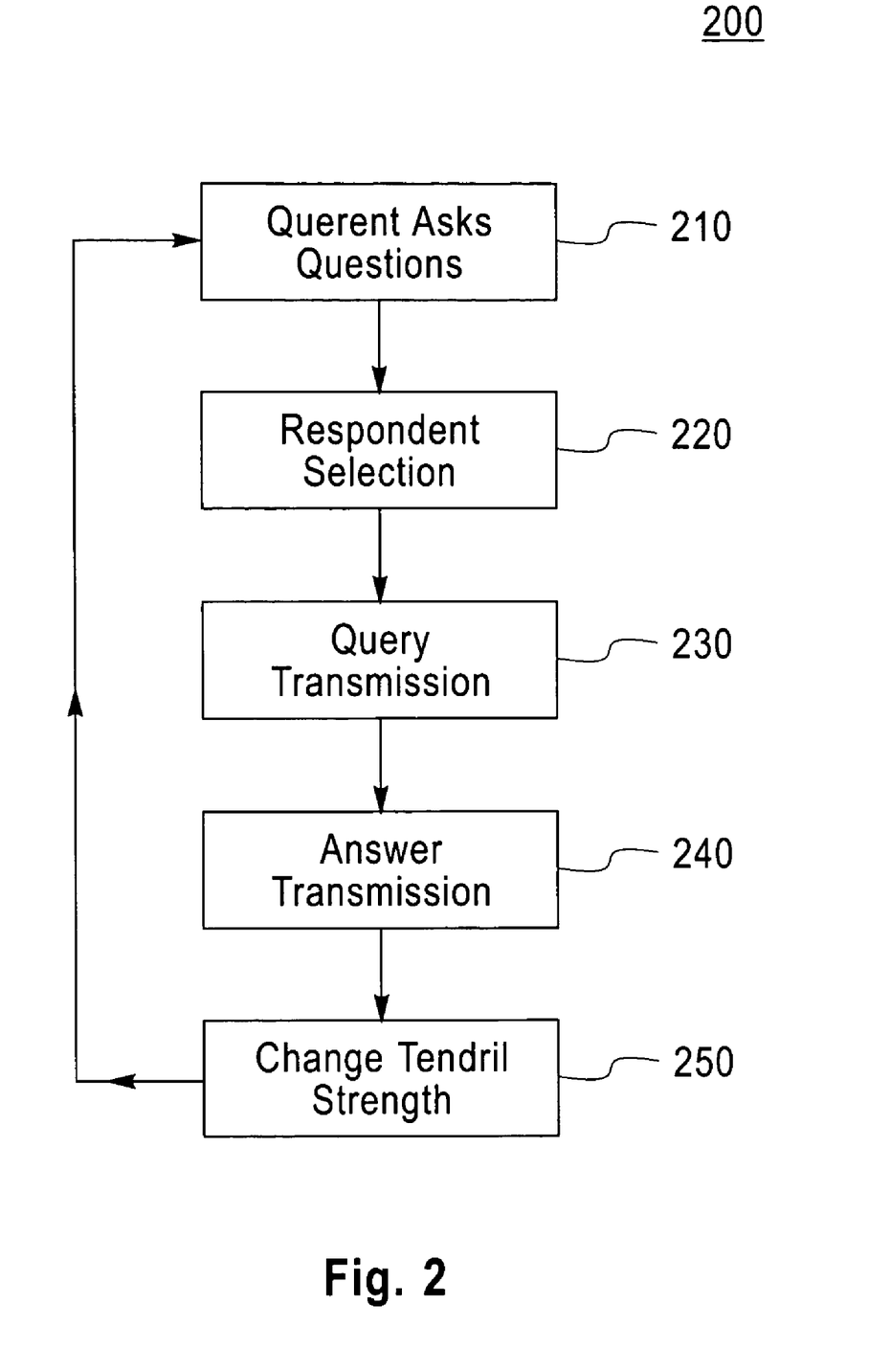
FIG. 2 is a flow chart showing one preferred embodiment of a query and answer transmission process.

FIG. 2 is a flow chart of one preferred process 200 that enables the operation of a TW.

In step 210, a querent asks a question. The queries 110Q are posed by any know machine query technique, e.g., voice, text, etc. The query 110Q might be parse using standard knowledge management techniques to determine the subject or other attributes of the query.

Potential responders 120 for this question are then chosen in step 220. For example, in a random selection, 5 random respondents 120 within a company may be selected. These recipients may be identified by e-mail addresses, instant message addresses, or by other means. In alternative embodiments, the responders are chosen because the have a strength value 140 above a certain threshold. In other embodiments, the responders 120 are chosen because they have a strength value above a threshold in a subject area (or other attributes (s)) related to the query 110Q. In still alternative embodiments, a vector analysis of the strength 120 is done. See FIG. 3 description.

In step 230, a question from the querent is sent to one or more respondents that were selected in step 220. This query sending may be performed using known methods for transmitting queries 110Q (textual, audio, visual, or multimedia) over a computer network from a querent 110 to a respondent 120.

In step 240, one or more of the selected responders 120 sends an answer to the querent 110, again by any well known technique.

In step 250, the strength S 140 associated with the connection path 130 is changed either manually or automatically. For example, if one responder 120 gave an excellent answer to a question/query 110Q, the user/querent 110 may increment the strength value using a computer interface. For example, a user/querent 110 may select an icon on the screen that cause an increase in the value of the strength (350 in FIG. 3), which is stored as a number(s) in a database 124. Alternatively, the TW software agent 150 may monitor the connection and determine that an answer has been sent, or determine that the quality of the answer is likely to be high, and change the value of S accordingly. The agent 150 may automatically estimate an assessment of answer quality by various means including an assessment of the length of the response, the amount of time a user had to wait for the response, or by examining keywords, grammar, and other content indicators in the response.

Subsequent queries 110Q may favor those responders 120 associated with high strength values. For example, in step 220, the system may determine the three potential respondents with the highest strength values and send the questions only to them. Respondents with low strength values may be dropped from a querent's TW and replaced with new random potential responders, which may or may not turn out to be useful in future queries. As this embodiment is used, the system 100 may retain respondents 120 with high strengths 140 and drop respondents with lower strengths 140. In this way, the network/set 120S of respondents 120 becomes "smarter" or more useful in the perception of the querent 110 or service provider 160.

Figure 3:
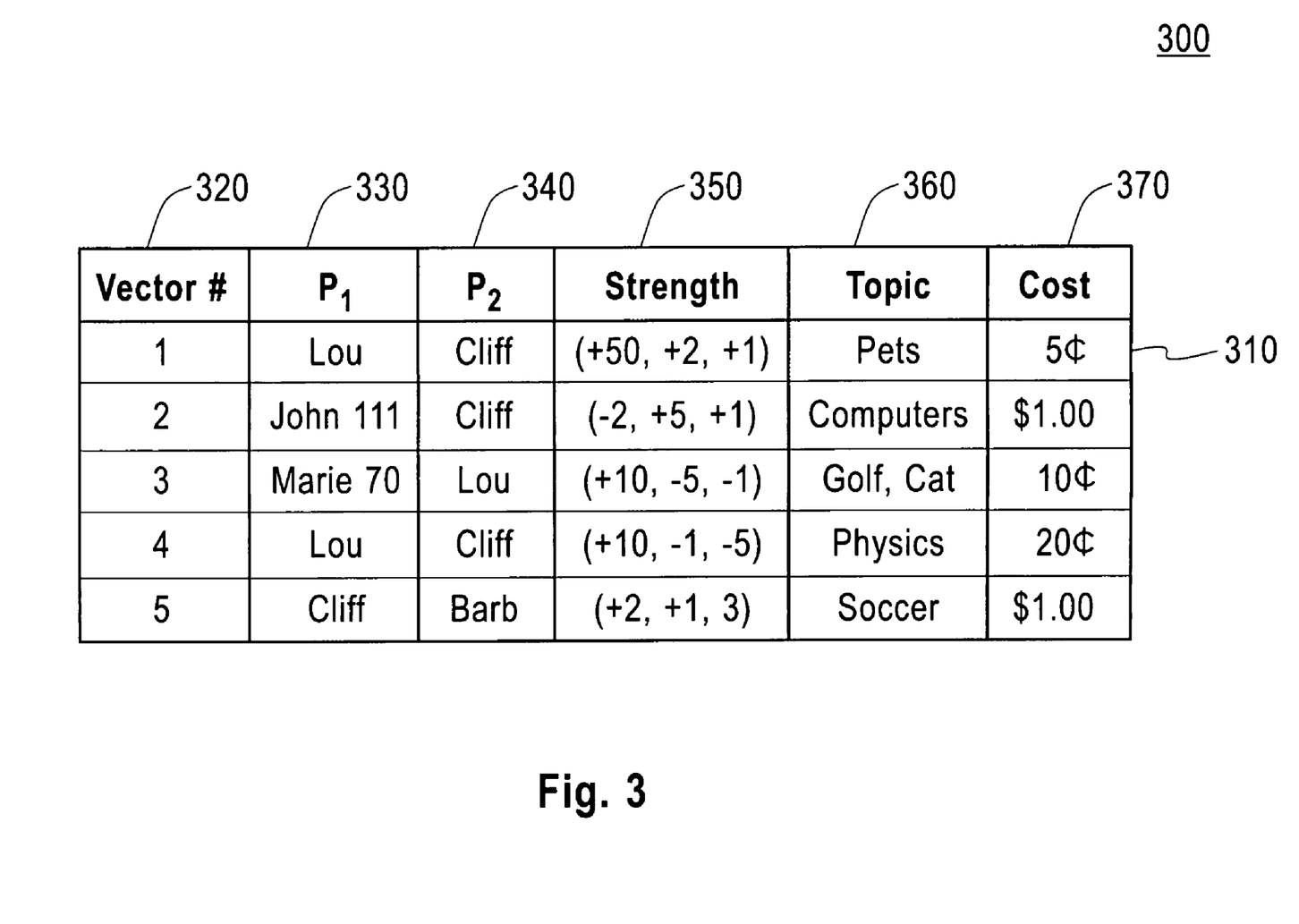
FIG. 3 is a diagram of one preferred database used to store information in the TW.

Data useful for operating the TW may be stored in a database 124 that resides on a user's client computer 112 or on another computer 124, such as a service bureau computer 124. FIG. 3 is a block diagram of one possible implementation of the database. Each line or record 310 of the database describes a strength path between querent and responder. The first column contains a strength vector identifier 320, such as a number. The second column contains an identifier 330 for one person, for example, the querent 110. The third column contains an identifier 340 for one person, for example, the responder 120. The fourth column contains the value of the strength, 140 of the strength path 130 between person 1 and person 2. These strength values 350 are also shown in FIG. 1 as S1, S2, S3 .... Note that these strength values may not need be single numbers but may be vectors. For example, a querent 110 or agent 150 may increment a three-dimensional vector in step 250 of FIG. 2 and store this vector in record 310 in database 124. The vector could include an assessment of the quality of an answer, an assessment of the speed of response, and an assessment of the empathy shown by the responder to the querent. If the strength values 140 are vectors, the TW may compare the magnitude or other composite characterization of the vectors when deciding upon which responder to use. Note that there might be several strength values 140 between the same querent 110 and responder 120 depending on other attributes of the vector 310, e.g., topic/subject matter 360 or cost 370. When the users adjusts the strength value using an icon, he may have multiple icons to increment the various parts of the vector, or answer questions relating to an assessment of the responders response in order to determine the value of the vector.

One or more topics may be stored in column 360. These topics characterize the interaction specified by the vectors in column 1. If a fee is charged for using the TW, for example, a fee charged for an answer given by a responder, the charge may be stored in column 370.

Figure 4:
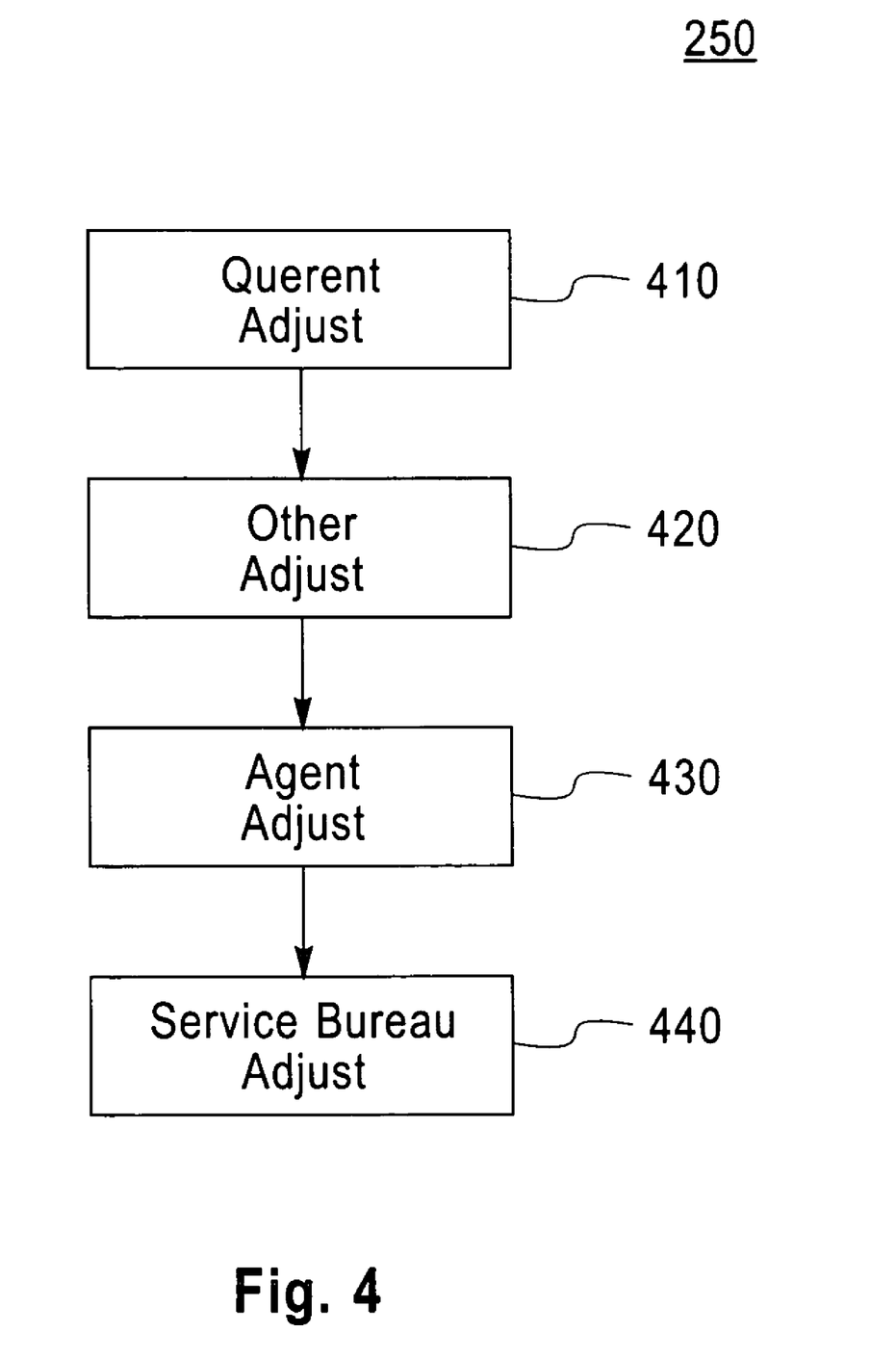
FIG. 4 is a flow chart of a strength changing process.

FIG. 4 is a flow chart of a process for step 250 in which the strength values 350 are changed. As an example, a responder may return an answer to a question. The querent may evaluate this answer along several dimensions. When the users adjusts 410 the strength value using an icon, he may have multiple icons, fields, or sliders to increment the various aspects of the response. For example, the querent may give the response a +50 for usefulness but a −5 for timeliness. These values may then be stored in 350. The querent may provide answers a short survey/questionaire (from the service 160) relating to an assessment of the responders 120 response in order to determine the value 350 of the vector.

Others may adjust the strength values 420. For example, a professor 123 may rate an answer as to accuracy, and the professor's strength value may reside in the database in addition to the querent's value. Alternatively, the strength value may be some weighted value representing both the querent's and the teacher's strength assessment. The software agent 150 may adjust the strength values 420. For example, an agent 123 may be able to automatically rate an answer given timeliness, the use of keywords, the use of correct grammar and so forth, and the agent's strength value may reside in the database in addition to the querent's value.

Alternatively, the strength value may be some weighted value representing both the querent's and the agent's strength assessment. The service bureau 160 may adjust the strength values 420. For example, a a service bureau 123 may rate an answer as to accuracy, and the bureau's strength value may reside in the database in addition to the querent's value. Alternatively, the strength value may be some weighted value representing both the querent's and the service bureau's strength assessment.

Figure 5:
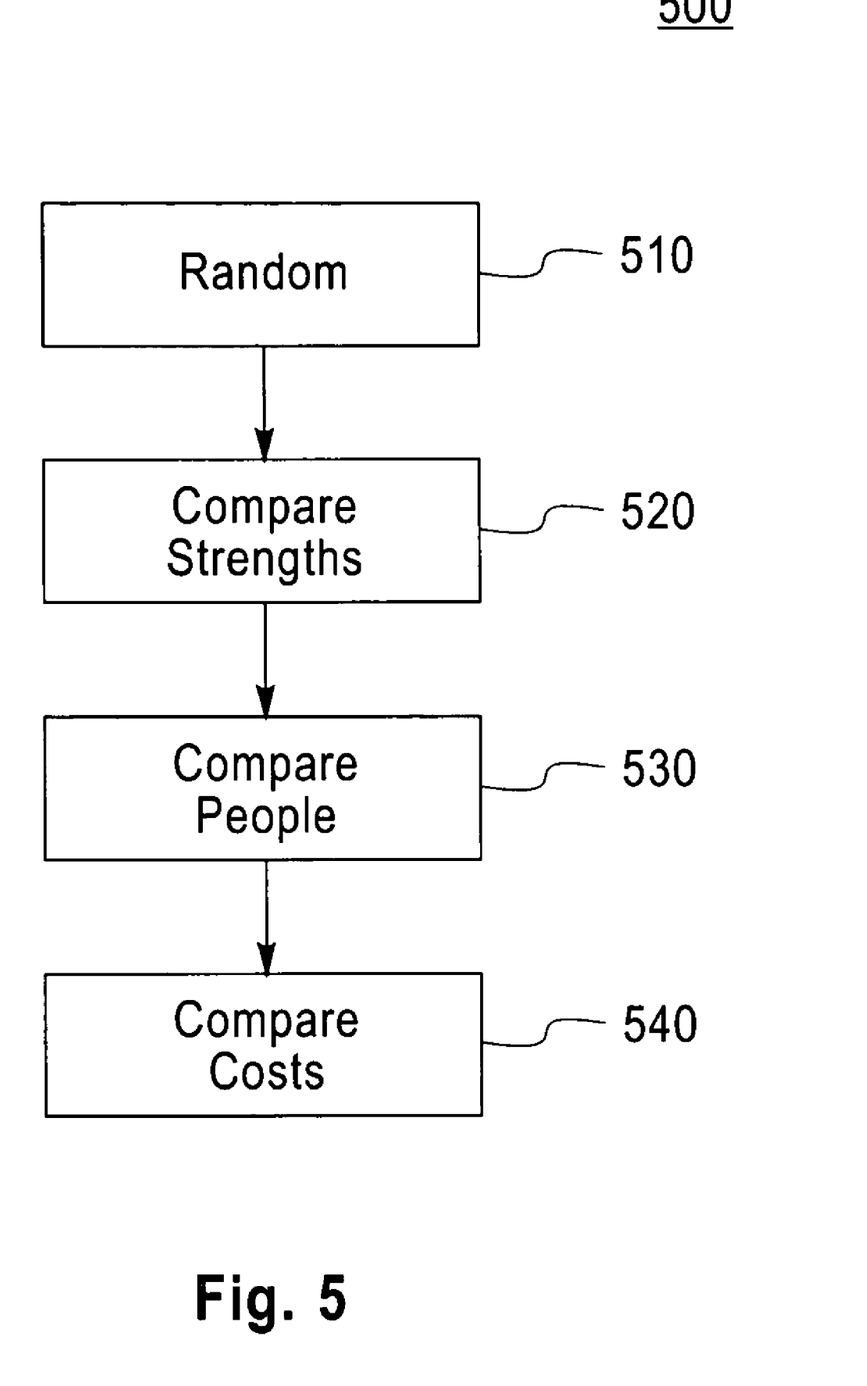
FIG. 5 provides is a flow chart of responder selection process.

FIG. 5 shows an embodiment of how potential responders may be selected in step 220 of FIG. 2. In some cases, it is useful to have some random selection of responders to encourage diverse ideas, working across company boundaries, and for other purposes. In step 510, one or more random potential responders is chosen. In step 520, strength values are used to determine potential responders. For example, the TW may examine a querent's previous strength paths by scanning records 310 in the database. If an existing strength path is value 360 is high, the responder corresponding to this strength path may be used again. In making this determination, the system may compute the magnitude of the strength values in 350 while also examining the topic field 360. In step 530, the system may also examine topics stored in column 360 to determine appropriate responders. For example, if a student asks a question about the US Constitution, the topic "US Constitution" may be scanned for in the database to help determine which responder to use. In step 540, the TW examine the fee charged in column 370. If a querent is concerned about cost, the TW may scan for previous low cost transaction and select responders from the set of low cost responders.

Thus, the system described herein represents a system and method comprising a querent seeking a responder (e.g. querent seeks information or an answer to a question), establishing a strength path (i.e. communications connection) between querent to one or more potential responders, providing a means for sending query between querent and one or more potential responders, a means for receiving a response from one or more responders, a means for assessing the quality of the response, a means for changing one or more strength path characteristics between querent and responders, and a means for selecting among potential responders based on strength path values.

A querent may be a person, software agent, group, company, or a service bureau. The responder may be a person, software agent, groups, company, or a service bureau. The strength path may be a vector associating an identifier, like an e-mail address, for the querent and the potential responder. One or more potential responders may be chosen randomly, particularly when the TW is first invoked. The identifier may be an e-mail address, a web URL, a person's name, a company's name, a software agent's name, a pseudonym for one or more people, or an alphanumeric string in a database 124. The querent or responder may remain anonymous. The sending may be via any of: e-mail, discussion board, web, phone, other network transmission. The assessing the quality is based on any of: a user-entered assessment (e.g. querent selects a "helpful" button if she judges answer to be helpful), automatic (e.g. a computer analysis of the response time, length of response, fog index of the response, biometric assessment of querent satisfaction), or quality assessment of other individuals such as friends, colleagues, managers, group of individuals, or a company.

For example, in step 420, a querent's colleagues, a teacher, or a review board may be sent a response and asked to evaluate it. The evaluation is returned and may affect the value of the strength 350 associated with this response. For example, a favorable response may increase the strength value.

The strength value may be changed based on the assessing of quality of the answer (e.g. a strength value is incremented by +1 if the quality is good). Subsequent queries are selectively routed along paths based on the strength of each path (e.g. high-strength paths are followed more or are preferred more than low-strength paths.) A fee may be charged based on the number of strength paths used. For example, a service bureau 160 may charge more if more strength paths are used. The strength path includes strength paths associated with one or more (neighboring) responders. For example, a user 110 can use his responder's 120 high-value strength paths 170 to access additional potential respondents. A fee may be changed based on the number of neighboring strength paths 170 used and access to responders.

Various automated techniques for determining quality of response may be used to automatically determine aspects of the strength 350 and may be used for determining which respondents to use in step 520. For example, the fog index is a proven method of analyzing written material to see how easy it is to read and understand. The steps required to calculate the fog index are known in the prior art and usually require an analysis of the number of words in a sentence, the number of big words (3 or more syllables), the average sentence length, and so forth. High scores for fog index indicate the writing sample in a response is too hard for most people to read. High values for the fog index might increase or decrease the strength values, depending on the querent.

The strength paths may be suggested by the system's software agent 160 (for example, the system may estimate the usefulness of certain strength paths and let a user use them). The network of strength paths may be used to determine centers of expertise or trustworthiness, for example, in an organization. A responder 120 or team of responders may be viewed to be valuable if their strength path values S 140 are high. The network can also be used to determine rewards for responders 120. The network can be used to identify areas in which new projects should start. If numerous questions are asked for which no one has answers or if the questions are continually asked, this may suggest a hot area for further research.

The TW has implications for students, teachers, schools, and companies. Part or all of strength paths network may be sold for a fee. The querent and responders may be any of: students, engineers, architects, lawyers, financial advisors, tax advisors, teachers, employees of a company, physicians in a physician network, users communicating on the Internet, anti-terrorist bureau, service bureau, help desk. The strength paths may be visualized (e.g. color and intensity are used to highlight high value strength paths). Authorities and concentrations of authorities may be identified by an analysis of strength paths. Certain strength paths may be protected (e.g. secured, made invisible, locked down temporarily, monitored for correctness, password protected, protected from abuse, etc.)

Users may often get quick answers and generate novel ideas using a TW. Through repeated use, users may evolve new ways of thinking about their computers as a tool for gaining insight and reasoning beyond the limits of their own intuition and abilities.

Uses for TW in education include a network of querents 110 and responders 120 that can be set up among students and teachers in a course. The teacher or a service provider 160 can mine the database to determine the student with the highest strength in the network for any given attributes, e.g., queries on subject matter of the course. Stronger strength values can be factored into the grade of the student/responder.

Uses for TW in corporations include a network of querents 110, e.g., employees and/or managers, and respondents 120, e.g., employees and/or managers. The managers and/or a service provider 160 can mine the database to determine strengths of employees for given attributes, e.g., speed of response, accuracy of response, number of correct responses, etc. Stronger strength values 140 can be a factor in the performance evaluation of the employee.

Uses for TW over a general network include a network of querents 110 that wish to evaluate or identify experts in certain areas, e.g., medicine, law, accounting, engineering, consulting, contracting, etc. The experts/respondents 120 are evaluated by mining data in the database according to certain criteria, e.g., number of satisfied querents, cost, timeliness of response, etc. Higher strength values for a respondent indicate a preference for this respondent among the querents 110 on the network. The respondents with higher strengths could demand high prices for their services than other respondents on the network. The information could also be mined by a service provider 160 that could provide access to a given respondent for a fee.

The foregoing description of the invention has been presented for purposes of illustration and description. It is not intended to be exhaustive or to limit the invention to the precise form disclosed, and other modifications and variations may be possible in light of the above teachings. The embodiments disclosed were chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

Responder selection in step 220 may typically employ first-level responders, but it may also select from among second-level responders, third-level responders, and so forth. These higher-level respondents are selected from a set of higher-level respondents using one or more of the following: the higher-level respondent with the highest strength value, the higher-level respondent with a strength value above a threshold, a random selection, a higher-level respondent with a strength value above a threshold in a specific subject area, and a cost of the response. The respondents may be selected from a set of higher-level respondents when one or more of the following conditions are met: a (first level) respondent does not provide an answer, a respondent makes a request to a higher-level respondent to respond, a querent makes a request to a higher-level respondent to respond, an agent 150 makes a request to a higher-level respondent to respond, a service bureau 160 makes a request to a higher-level respondent to respond. In this manner, useful answers may be obtained by the querent, for example, when a first-level responder is unavailable or does not know the answer to a question.

Figure 6:
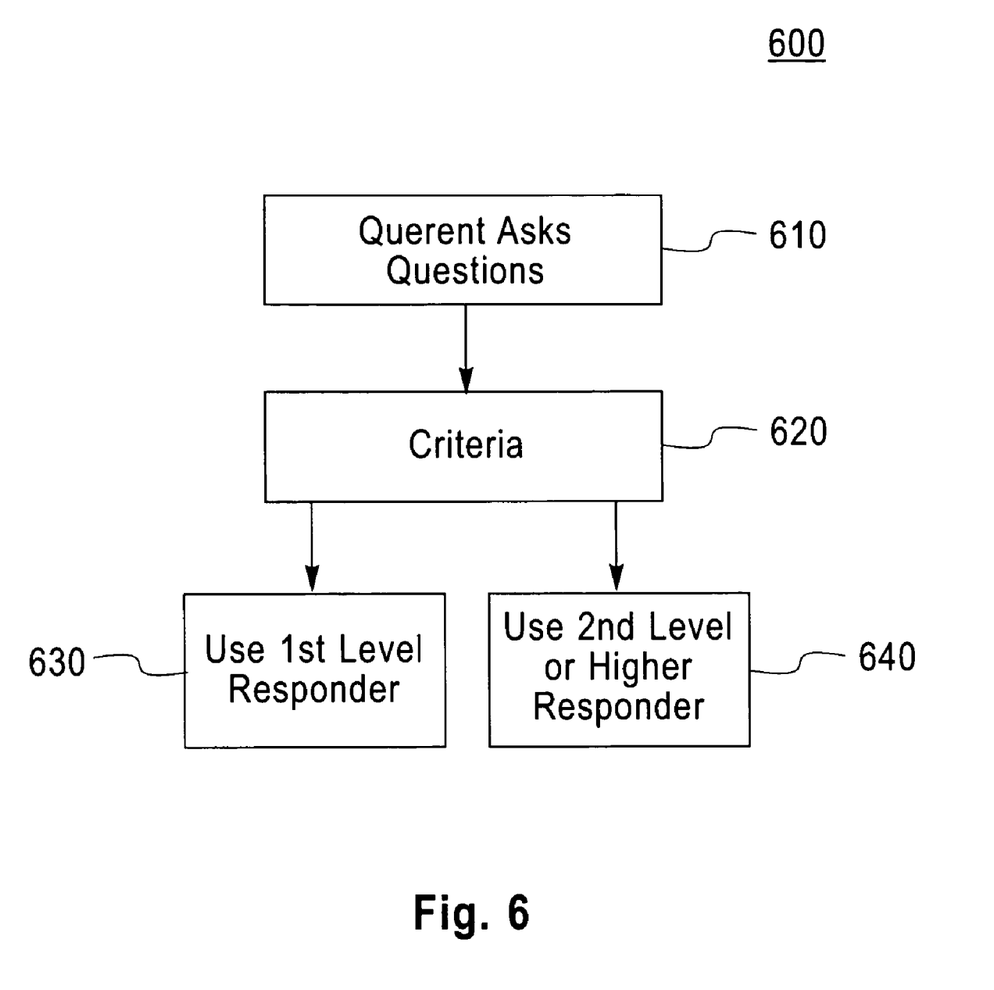
FIG. 6 provides a flow chart of the higher-level responders selection process.

The system may determine a second-level responder, or higher-level responders, for a querent by an analysis (performed in step 640) of the table in FIG. 3. For example, the system may determine that "Cliff" is a respondent P2 in column 340 for querent P1, who is identified as "Lou" in column 330. The system may now scan for respondents P2 (Barb) for Cliff when Cliff appears in column 330. Thus, those people identified (Barb) in column 340 for Cliff are second-level responders to Lou. It is possible that if Cliff has provided high-quality answers to Lou on particular subjects then Cliff's respondents (Barb) may have similar interests, dispositions, and expertise as Cliff and thus would be potentially useful to help Lou with a question or other interaction. Alternatively, Cliff could provide Lou with some or all of Cliff's database 124 upon request, for receiving a fee (e.g., by selling all or part of the database, or by granting access for free or with some other conditions (e.g., if Lou is a member of Cliff's club or newsletter)).

Through continual use of the TW, the system evolves a set of communications channels that lead to an efficient and perhaps enjoyable means for information dissemination that may be used, for example, on the job, for hobbyists, for entertainment purposes, for students, for help desks, for financial transactions, and for auction and barter. In a financial, barter, or auction scenario, querents and responders may comprise potential sellers and potential buyers for goods and services. A querent may offer a good or service in the same manner as described in FIG. 2 (step 210). For example, the querent seller (buyer) would ask: Does any one want to buy a computer? (Does anyone have a computer for sale?) A potential buyer (seller) may be selected in the same manner as described in step 220 for the selection of a responder. In this manner, a fluid and efficient set of communication channels evolves between potential sellers and potential buyers. In buyer/seller scenarios, the topic 360 may represent, for example, a good or service category such as antiques, computers, Picasso paintings, science-fiction books, computer services, gold jewelry, or any other good or product. Likewise services can be bought and sold. These services include: financial, engineering, architectural, medical, legal, consulting, recreational, marketing, sales, writing, entertainment, real estate, tax, employment, and/or any other service. In step 240, the potential buyer transmits an offer for a goods and services. The strength values 350 may characterize such items as the timeliness, clarity of offer, and trustworthiness of a potential buyer/seller. In this use there can also be levels of buyers or sellers. Note that in different embodiments of the invention, the buyer could be the querent (Is this item for sale?) or the respondent (Yes I'm looking for an antique.) In like manner, the seller can also be the querent (Is anyone interested in my antiques?) or the respondent (Yes I have antiques to sell.)

FIG. 6 is a flow chart of a higher-level selection process 600 for selecting higher level responders. In step 610, as in step 210, a querent asks a question.

In step 620, various criteria are applied to determine if higher-level responders are used. If, it is determined there are no reasons to access higher level responders, the process 600 stops at a first level responder 630 as in FIG. 2.

However, applying the criteria in step 620 might require that higher level responders are selected. One examples of these criteria is if a respondent does not provide an answer, for example, because he is on vacation and away from the computer. Other criteria may be employed to determine if higher-level responders are used in step 640. Other criteria include: a respondent making a request to a higher-level respondent to respond, a querent making a request to a higher-level respondent to respond, an agent making a request to a higher-level respondent to respond, a service bureau making a request to a higher-level respondent to respond. Other criteria for selecting higher-level responders, such as an assessment of strength values, may be used as described in FIG. 2 which outlines the process for first-level responders. For example, a higher level responder might be selected if the higher level responder has a strength value above a threshold in a given area or if their cost is low.

Both the querents and respondents may remain anonymous. This may be implemented by not revealing identifiers 330 and 340 to users of the system. Anonymity may be useful to avoid bias or prejudice on the part of responders and for privacy or other reasons.

The respondent may be a "virtual responder." For example, a querent may ask a querent of "Mr. Answer Man," or "Dr. Smith," who in reality is a virtual entity comprising several responders. This virtual entity may be reimbursed, rewarded, and given jobs. For example, if Mr. Answer Man (comprising 5 individuals) answers 10 questions satisfactorily and he's given a reward of $10. Each responder in the virtual responder may be given ⅕ or $2 for providing this answer as a service.

A service bureau 160 may providing a service for assessing following: centers of competency in a group, centers of lack of competency in a group, teams to be built from responders. The service may provide this information by mining the data in records 310 in the table in FIG. 3. For example, if Lou and Cliff have a history of providing high-quality answers as gleaned from their high strength values 350 or sheer number of vectors 320 and/or ability to make money (as seen in the costs 370) they may be deemed to be centers of competency or trustworthiness. On the other hand, for example, if Lou and Cliff have a history of providing poor answers as gleaned from their low strength values 350 or few number of vectors 320 and/or ability to make money (as seen in the costs 370), they may be deemed to be centers of low competency or low trustworthiness in general or for particular topics 360.

Figure 7:
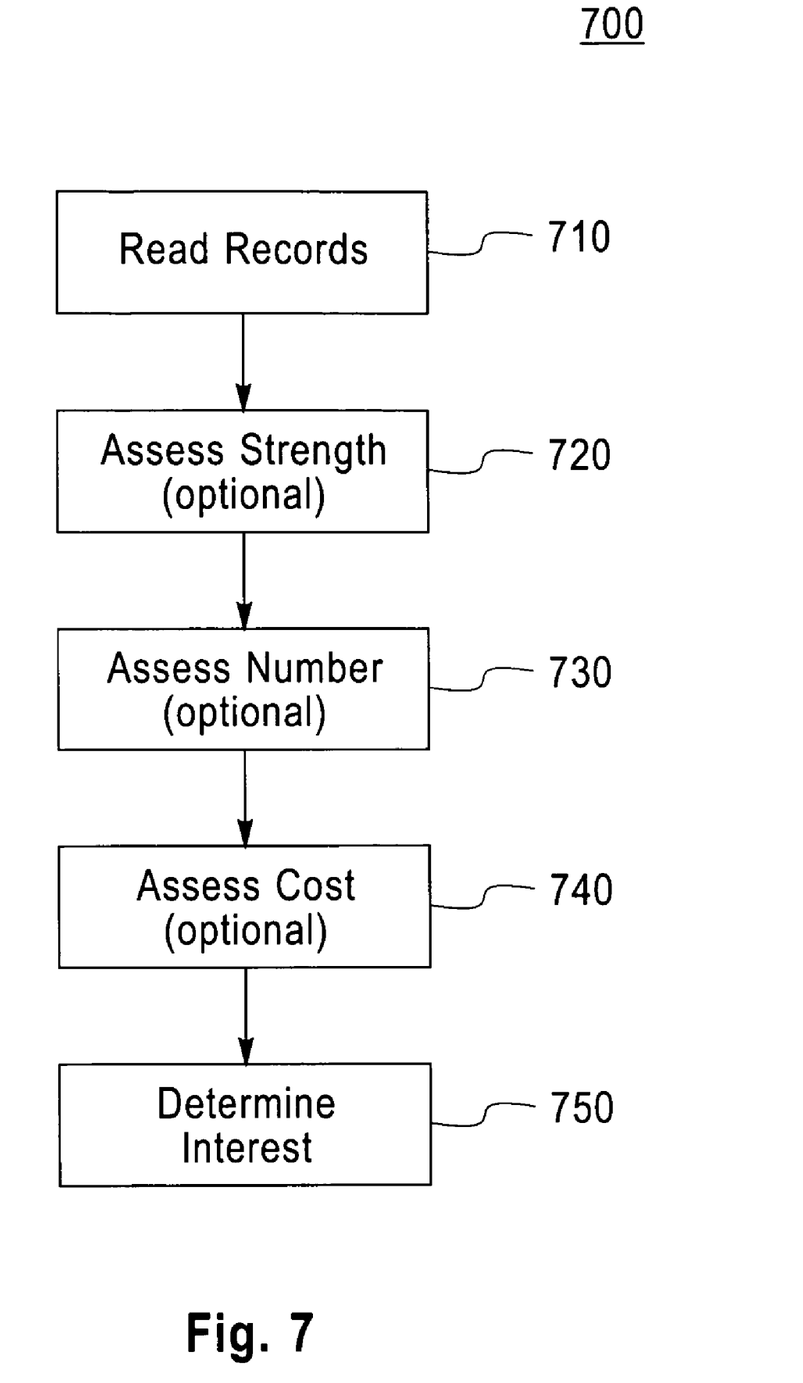
FIG. 7 provides a flow chart of a database mining process.

FIG. 7 is a flow chart of a mining process 700 showing of how such centers of interest or activity (e.g., competency) or lack of interest or activity (or competency) may be mined from the table in FIG. 3. In step 710, service bureau 160 or agent 150 reads records 310. In step 720, the composite strength for a particular respondent 340 is computed. For example, this may be an average of the strengths 350 of a set of vectors 320 for the respondent 340 for a particular topic 360. There are other known techniques for determining these composite strengths, e.g., mode, median, measures of central tendency, or other statistics. Alternatively, or in addition to, step 730 computes the number of responses for the respondent 340. Again, alternatively or in addition to, step 740, a cost measure (e.g., the total or average cost) is computed for all the costs for respondent 340. Therefore, each of the steps 720, 730, and 740 gives a measure of some level of competency or interest or activity of a given respondent or querent. These steps can optionally be used together or separately to determine the competency or selectability of the respondent (or even querent) in step 750. In step 750, a competency value is computed that describes the overall competency or trustworthiness of a respondent. This competency may be computed in general or for one or more particular topics for a respondent. For example, the competency value may be a function of the various strengths, number of responses, and costs for the various responses. Thus, centers of competency, comprising an individual, groups of individuals, or virtual responders may be determined and provided to an employer of the individuals. Using this information, the service bureau may also suggest the formation of teams comprising high-competency responders for new projects or other purposes.

I claim:

1. A computerized method for data access comprising the steps of:

selecting one or more sets of respondents to respond to one or more queries from a querent by using a strength value between the querent and one or more of the respondents in the set;

receiving one or more responses to the query from one or more of the respondents;

updating the strength values of the respective respondent by an assessment of the response;

iteratively evolving updated connections for future queries, based at least in part on said updated strength values; and storing said updated connections in a data structure such that a computer can access said data structure to obtain useful responses to said future queries.

2. A method of providing a service for accessing responses to queries comprising the steps of:

receiving one or more queries from one or more querents;

selecting one or more sets of respondents to respond to one or more of the queries by using a strength value between the querent and one or more of the respondents in the set;

receiving one or more responses to the query from one or more of the respondents;

updating the strength values of the respective respondent by an assessment of the response;

iteratively evolving updated connections for future queries, based at least in part on said updated strength values;

storing said updated connections in a data structure such that a computer can access said data structure to obtain useful responses to said future queries; and charging a fee for, at least, access to said database for purposes of obtaining said useful responses.

3. A method of providing a service, as in claim 1, where the fee is one or more of the following: a charge based on the number of strength paths used to respond to the query, a charge based on the strength of one or more of the strength paths used to respond to the query, a number of responses received, a charge for one or more records in the database, a charge for a number of neighboring strength paths used, a charge for one or more strengths of one or more of the neighboring strength paths, a charge to identify centers of expertise, a charge to identify effectiveness of one or more of the responders, and a charge to access one or more of the responders.

* * * * *